United States Patent
Collins et al.

(10) Patent No.: US 11,103,343 B2
(45) Date of Patent: Aug. 31, 2021

(54) INTRAOCULAR LENSES HAVING OPEN-LOOP HAPTIC STRUCTURES

(71) Applicant: Alcon Inc., Fribourg (CH)

(72) Inventors: Stephen John Collins, Fort Worth, TX (US); Jonathan David McCann, Van Alstyne, TX (US); Jian Liu, Keller, TX (US); Michael Lee Mangum, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 113 days.

(21) Appl. No.: 16/144,378

(22) Filed: Sep. 27, 2018

(65) Prior Publication Data

US 2019/0091009 A1    Mar. 28, 2019

Related U.S. Application Data

(60) Provisional application No. 62/563,989, filed on Sep. 27, 2017.

(51) Int. Cl.
*A61F 2/16* (2006.01)

(52) U.S. Cl.
CPC .............. *A61F 2/1613* (2013.01); *A61F 2/16* (2013.01); *A61F 2/1694* (2013.01); *A61F 2002/1681* (2013.01)

(58) Field of Classification Search
CPC ...... A61F 2002/1681; A61F 2002/1682; A61F 2002/16903; A61F 2002/1686; A61F 2/1613; A61F 2/16; A61F 2/1694
See application file for complete search history.

(56) References Cited

U.S. PATENT DOCUMENTS

| | | | | |
|---|---|---|---|---|
| 4,434,515 A * | 3/1984 | Poler | ......................... | A61F 2/16 623/6.41 |
| 4,437,194 A * | 3/1984 | Hahs | ......................... | A61F 2/16 623/6.51 |
| 4,955,902 A * | 9/1990 | Kelman | ................. | A61F 2/1602 623/6.54 |
| 6,228,115 B1 * | 5/2001 | Hoffmann | ............. | A61F 2/1616 623/6.49 |
| 9,078,744 B2 * | 7/2015 | Van Noy | ................. | A61F 2/1613 |
| 2006/0047340 A1 * | 3/2006 | Brown | ................... | A61F 2/1648 623/6.13 |
| 2008/0269881 A1 * | 10/2008 | Simpson | ............... | A61F 2/1613 623/6.17 |
| 2010/0094415 A1 * | 4/2010 | Bumbalough | ......... | A61F 2/1694 623/6.51 |
| 2012/0130488 A1 * | 5/2012 | Doraiswamy | .............. | A61F 2/16 623/6.43 |

FOREIGN PATENT DOCUMENTS

DE    4030005    *  3/1992   ............... A61F 2/16

* cited by examiner

*Primary Examiner* — Jennifer Dieterle
*Assistant Examiner* — Tiffany P Shipmon

(57) ABSTRACT

An ophthalmic device includes an optic including an optic axis and an open-loop haptic structure coupled with the optic. The open-loop haptic structure includes a pair of open loops, the pair of open loops comprising a first open loop and a second open loop. At least a portion of the first open loop extends in a first angular direction. At least a portion of the second open loop extends in a second angular direction, the second angular direction being opposite the first angular direction.

16 Claims, 5 Drawing Sheets

INTRAOCULAR LENSES HAVING OPEN-LOOP HAPTIC STRUCTURES

FIELD

The present disclosure relates generally ophthalmic lenses and, more particularly, to intraocular lenses having open loop haptic structures.

BACKGROUND

Intraocular lenses (IOLs) may be implanted in patients' eyes to replace a patient's natural lens. An IOL typically includes (1) an optic that corrects the patient's vision (e.g., typically via refraction or diffraction), and (2) haptics that constitute support structures that hold the optic in place within the patient's eye (e.g., within capsular bag). In general, a physician selects an IOL for which the optic has the appropriate corrective characteristics for the patient. During ophthalmic surgery, often performed for conditions such as cataracts, the surgeon implants selected IOL by making an incision in the capsular bag of the patient's eye (a capsulorhexis) and inserting the IOL through the incision. Typically, the IOL is folded for insertion into the capsular bag via a corneal incision and unfolded once in place within the capsular bag. During unfolding, the haptics may expand such that a small section of each bears on the capsular bag, retaining the IOL in place.

Although existing IOLs may function acceptably well in many patients, they also have certain shortcomings. For example, existing IOL design may include haptics that cause striae, or folds, in the posterior capsular bag. Such striae may result from the haptics having a relatively small angle of contact with the capsular bag. Because striae may negatively impact patient outcomes (e.g., by resulting in increased posterior capsular opacification (PCO) by providing a mechanism for the growth and/or migration of cells), haptic designs that reduce striae are desirable. Moreover, such designs should also have a volume and foldability conducive to maintaining acceptably small incision sizes (e.g., 3 mm or less) as larger incision may adversely affect the patient's recovery.

Accordingly, what is needed is an improved IOL that may address PCO (e.g., by reducing striae) without significantly complicating implantation.

SUMMARY

An ophthalmic device includes an optic including an optic axis and an open-loop haptic structure coupled with the optic. The open-loop haptic structure includes a pair of open loops, the pair of open loops comprising a first open loop and a second open loop. At least a portion of the first open loop extends in a first angular direction. At least a portion of the second open loop extends in a second angular direction, the second angular direction being opposite the first angular direction.

In certain embodiments, the open-loop haptic structure described herein may result in fewer striae and reduced PCO, yet may be relatively easily implanted. Consequently, performance of the ophthalmic device may be improved.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

The skilled person in the art will understand that the drawings, described below, are for illustration purposes only. The drawings are not intended to limit the scope of the applicant's disclosure in any way.

DETAILED DESCRIPTION

The exemplary embodiments relate to ophthalmic devices such as intraocular lenses (IOLs). The following description is presented to enable one of ordinary skill in the art to make and use the invention and is provided in the context of a patent application and its requirements. Various modifications to the exemplary embodiments and the generic principles and features described herein will be readily apparent. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. Thus, the present invention is not intended to be limited to the embodiments shown, but is to be accorded the widest scope consistent with the principles and features described herein.

In general, the present disclosure relates to an ophthalmic device that includes an optic including an optic axis and an open-loop haptic structure coupled with the optic. The open-loop haptic structure includes a pair of open loops, the pair of open loops comprising a first open loop and a second open loop. At least a portion of the first open loop extends in a first angular direction. At least a portion of the second open loop extends in a second angular direction, the second angular direction being opposite the first angular direction.

Figure 1A:
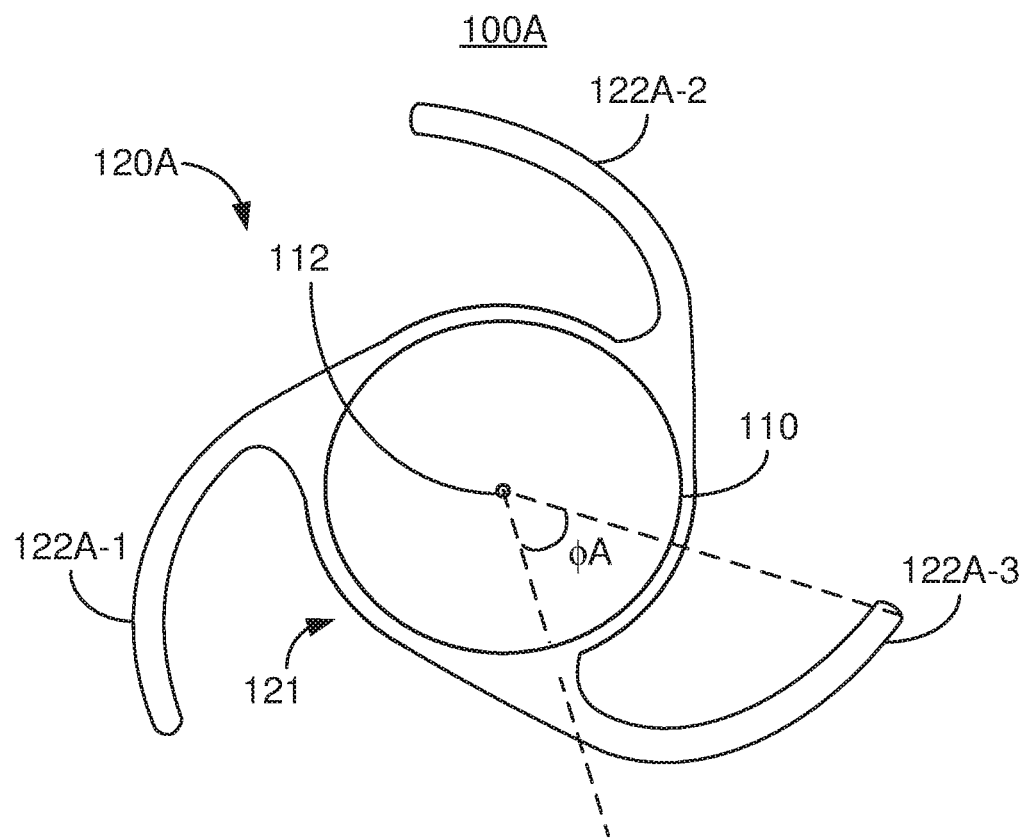
FIGS. 1A-1B depict plan and side views of an exemplary embodiment of an ophthalmic device having an open-loop haptic structure.
Figure 1B:
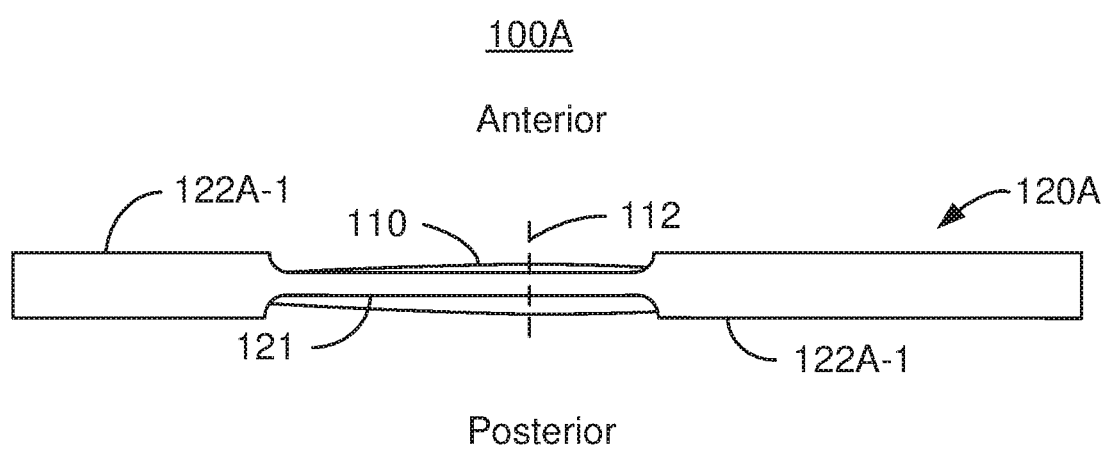

FIGS. 1A-1B depict plan and side views, respectively, of an exemplary embodiment of an ophthalmic device 100A including an optic 112 and an open-loop haptic structure 120A. For simplicity, the ophthalmic device 100A is also referred to as an IOL 100A. FIGS. 1A-1B are not to scale and not all components may be shown.

The optic 110 is an ophthalmic lens 110 that may be used to correct a patient's vision. For example, the optic may be a refractive and/or diffractive lens. The optic 110 may be a monofocal lens, multifocal lens and/or a toric lens. The anterior and/or posterior surface of the optic 110 may thus have features including but not limited to a base curvature and diffraction grating(s). The optic 110 may refract and/or diffract light to correct the patient's vision. The optic 110 has an optic axis 112 that is out of the plane of the page in FIG. 1A. The optic 110 is depicted as having a circular footprint in the plan view of FIG. 1A. In other embodiments, the optic 110 may have a differently shaped footprint. In some embodiments, the optic 110 may also include other features that are not shown. The optic 110 may be formed of one or more of a variety of flexible optical materials. For example, the optic 110 may include but is not limited to one or more of silicone, a hydrogel and an acrylic such as AcrySof®.

The haptic structure 120A is a support structure used to hold the ophthalmic device 100A in place in the capsular bag of a patient's eye (not explicitly shown). The haptic structure 120A includes a frame 121 (or ring) and open loops 122A-1, 122A-2 and 122A-3 (collectively or generically 122A). The haptic structure 120A is thus an open-loop haptic structure.

The frame 121 couples the haptic structure haptic 120A with the optic 110. The inner portion of the frame 121 may be desired to match the shape of the optic 110. Thus, the inner edge of the frame 121 shown as circular in FIG. 1A may have a different shape. The outer edge of the frame 121 can but need not match the inner edge. In some embodiments, the haptic structure 120A and the optic 110 may be molded together. Thus, the optic 110 and haptic 120A may form a single monolithic structure. In other embodiments, the frame 121 may be otherwise attached to the optic 110. For example, the frame 121 may be bonded to or molded around a preexisting optic 110. Alternatively, the frame may be omitted. In such a case, the open loops, or arms, 122A are coupled directly with the optic 110. The open loops 122A may be attached to the optic 110 or molded together with the optic 110.

The open loops 122A-1, 122A-2 and 122A-3 may retain the IOL 100A in position in the patient's eye by contacting the capsular bag. Each of the loops 122A spans an angle, $\phi A$. In certain embodiments, the angle $\phi A$ is at least sixty degrees. The open loops 122A-1, 122A-2 and 122A-3 may be evenly distributed around the optic axis 112. For example, each open loop 122A may be approximately one hundred and twenty degrees (plus or minus not more than ten degrees) from another open loop. In some embodiments, more open loops may be present. In such embodiments, the open loops are still evenly distributed around the optic axis 112. The angle between open loops may simply be reduced to accommodate more loops. Although the open loops 122A have the same length, in other embodiments, one or more of the loops 122A-1, 122A-2 and 122A-3 may have a different length. Further, the open loops 122A are curved in the same direction. Because of their configuration, combined the loops 122A contact the capsular bag over a large angle. The capsular bag may thus be extended over a larger volume. The loops 122A-1 and 122A-2 may thus stretch the capsular bag over a larger region. Moreover, the extension of the bag may have improved circular symmetry. This may increase stability, reduce striae and, therefore, reduce the incidence of PCO.

As illustrated in in FIG. 1B, the haptic structure 120A may include sharp corners. Both the loops 122A and the frame 121 may have sharp edges. As a result, the optic 110 may be surrounded on all sides by sharp edges. These sharp edges may also reduce the probability of cells migrating to the optic 110 from any side. Again, the incidence of PCO may be reduced.

Use of the IOL 100A may improve patient outcomes. The larger number of arms 122A that curve in the same direction, span a collectively large angle and are evenly distributed around the capsular bag allow haptic structure to contact a larger portion of and better extend the capsular bag. This may not only improve the axial and rotational stability of the IOL 100A, but also reduce the formation of striae (wrinkles) in the capsular bag. This may mitigate or prevent PCO. Sharp edges for the closed-loop haptic structure 120A may further reduce PCO. Thus, performance of the IOL 100A may be further improved.

Figure 2A:
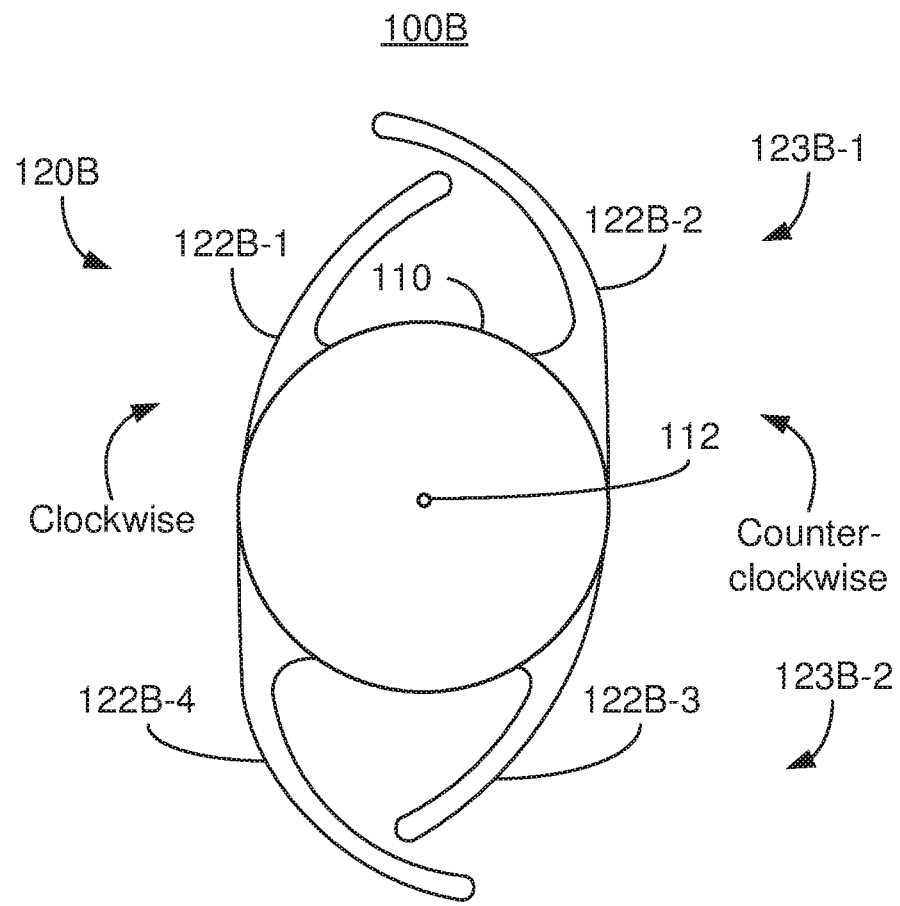
FIGS. 2A-2B depict plan and side views of another exemplary embodiment of an ophthalmic device having an open-loop haptic structure.
Figure 2B:
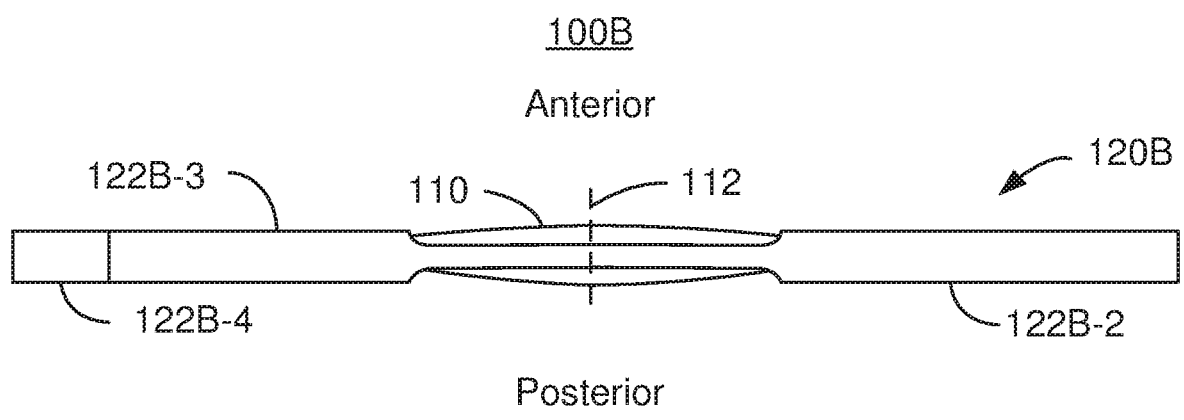

FIGS. 2A and 2B depict plan and side views, respectively, of another exemplary embodiment of an ophthalmic device 100B having an optic 110 and an open-loop haptic structure 120B. For simplicity, the ophthalmic device 100B is also referred to as an IOL 100B. The IOL 100B is analogous to the IOL 100A. Consequently, analogous components have similar labels. Thus, the IOL 100B includes an optic 110 and open-loop haptic structure 120B that are analogous to the optic 110 and open-loop haptic structure 120A. Because optic 110 of IOL 100B is substantially the same as the optic 110 of IOL 100A, the optic 110 of IOL 100B will not be separately described with regard to FIGS. 2A and 2B. For clarity, FIGS. 2A and 2B are not to scale and not all components may be shown.

In the depicted embodiment, the loops 122B are coupled with the optic 110. Thus, a frame analogous to the frame 121A has been omitted. In other embodiments, a frame may be present. In some embodiments, the haptic structure 120B and the optic 110 may be molded together. Thus, the optic 110 and haptic 120B may form a single monolithic structure. In other embodiments, the haptic 120B may be otherwise attached to the optic 110. For example, the loops 122B may be bonded to or molded around a preexisting optic 110.

The loops 122B may be divided into pairs 123B-1 and 123B-2 (collectively or generically 123B). The pair 123B-1 includes loops 122B-1 and 122B-2. The pair 123B-2 includes loops 122B-3 and 122B-4. The pairs of loops 123B retain the IOL 100B in position in the patient's eye. Although two opposing pairs 123B are shown, in another embodiment, another number of pairs may be included. Such pair(s) may but need not be opposite another pair. At least the loops 122B-2 and 122B-4 contact the capsular bag. Portions of the shorter loops 122B-1 and 122B-3 may also contact the capsular bag. The shorter loops 122B-1 and 122B-3 in a pair extend in the opposite direction from the longer loops 122B-2 and 122B-4. Thus, the loops 122B-1 and 122B-3 may curve in the clockwise direction while the loops 122B-2 and 122B-4 may curve in the counter-clockwise direction. Because of the directions of curvature and lengths differ, the loops 122B-1 and 122B-3 end between a portion of the loops 122B-2 and 122B-4, respectively, and the optic 110. When the loops 122B are compressed by the capsular bag, the ends of the shorter loops 122B-1 and 122B-3 may abut portions of the longer loops 122B-2 and 122B-4, respectively. Thus, the shorter loops 122B-1 and 122B-3 may interlock with the longer loops 122B-2 and 122B-4, respectively, preventing the longer loops 122B-2 and 122B-4 from collapsing when compressed radially. Thus, the stability of the IOL 100B may be improved. Further, the loops 122B may better extend the capsular bag because of this configuration. Striae and PCO may thus be reduced.

As can be seen in FIG. 2B, the haptic structure 120B includes sharp corners. As a result, the optic 110 may be surrounded on all sides by sharp edges. PCO may be reduced or eliminated by the haptic structure 120B.

The IOL 100B may share some or all of the benefits of the IOL 100A. The short loops 122B-1 and 122B-3 of each pair 123B may prevent the longer loops 122B-2 and 122B-4, respectively, from collapsing when compressed by the capsular bag. This may improve the stability of the IOL 100B, reduce striae in the capsular bag, and mitigate or prevent PCO. Sharp edges for the closed-loop haptic structure 120B may further reduce PCO. Thus, performance of the IOL 100B may be improved.

Figure 3A:
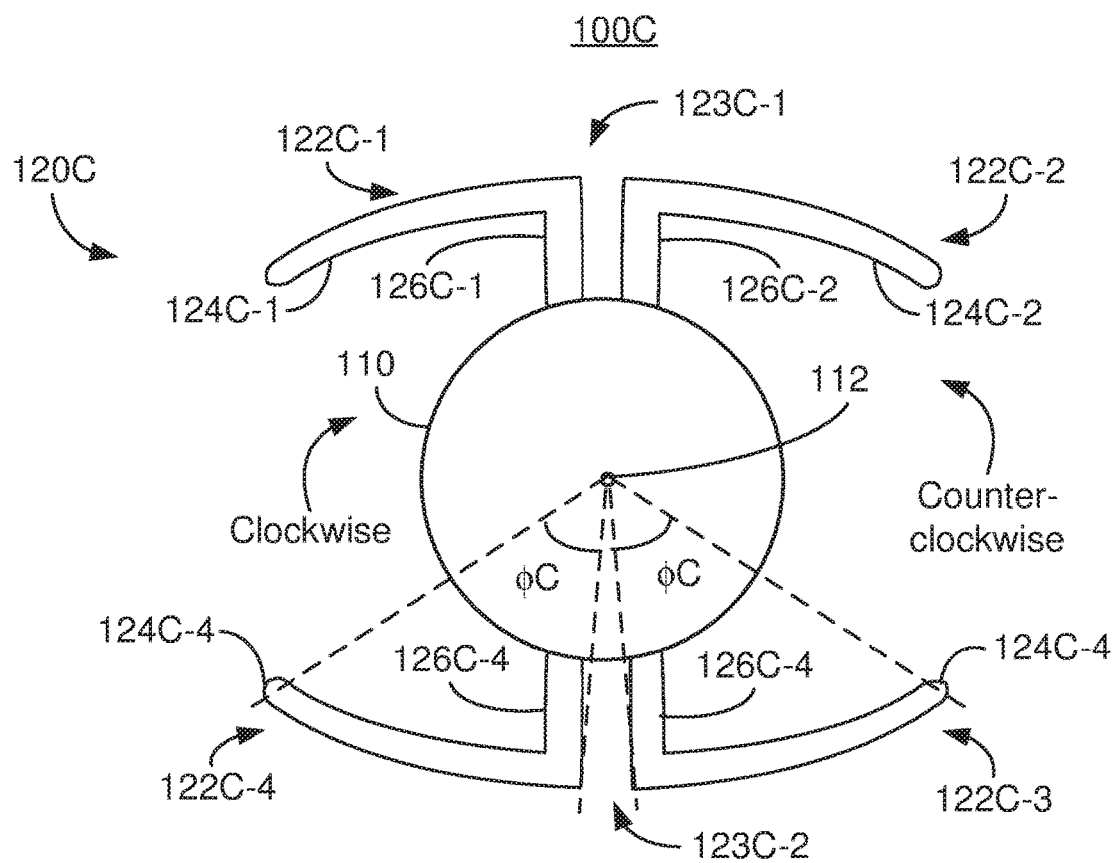
FIGS. 3A-3B depict plan and side views another exemplary embodiment of an ophthalmic device having an open-loop haptic structure.
Figure 3B:
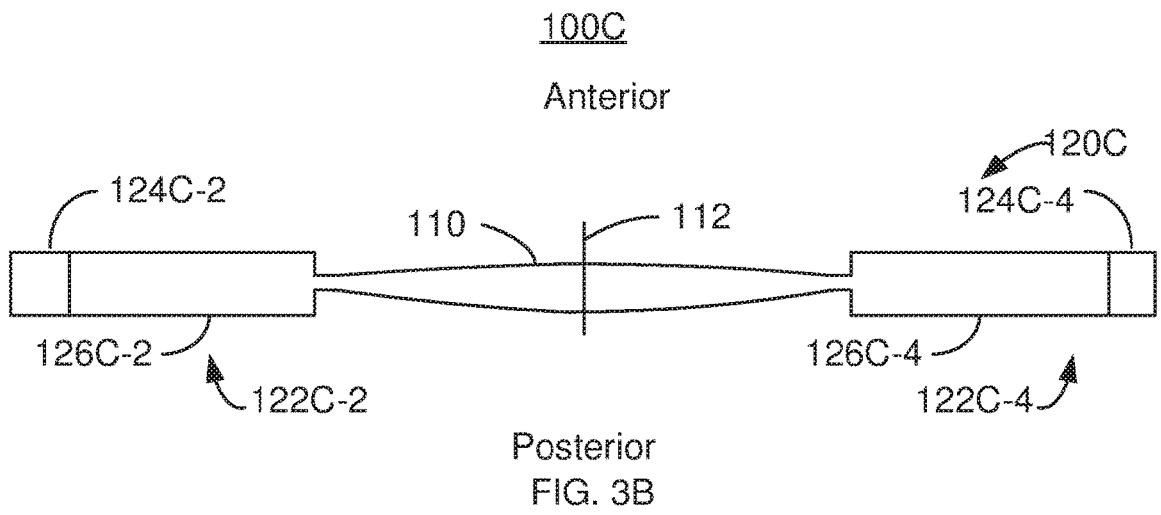

FIGS. 3A and 3B depict plan and side views, respectively, of another exemplary embodiment of an ophthalmic device 100C having an optic 110 and an open-loop haptic structure 120C. For simplicity, the ophthalmic device 100C is also referred to as an IOL 100C. The IOL 100C is analogous to the IOL 100A. Consequently, analogous components have similar labels. Thus, the IOL 100C includes an optic 110 and open-loop haptic structure 120C that are analogous to the optic 110 and open-loop haptic structure 120A. Because optic 110 of IOL 100C is substantially the same as the optic 110 of IOL 100A, the optic 110 of IOL 100C will not be separately described with regard to FIGS. 3A and 3B. For clarity, FIGS. 3A and 3B are not to scale and not all components may be shown.

In the embodiment shown, the loops 122C are coupled with the optic 110. Thus, a frame analogous to the frame 121A has been omitted. In other embodiments, a frame may be present. In some embodiments, the haptic structure 120C and the optic 110 may be molded together. Thus, the optic 110 and haptic 120C may form a single monolithic structure. In other embodiments, the haptic 120C may be otherwise attached to the optic 110. For example, the loops 122C may be bonded to or molded around a preexisting optic 110.

The loops 122C may be divided into pairs 123C-1 and 123C-2 (collectively or generically 123C). The pair 123C-1 includes loops 122C-1 and 122C-2. The pair 123C-2 includes loops 122C-3 and 122C-4. The pairs of loops 123C retain the IOL 100C in position in the patient's eye. Although two opposing pairs 123C are shown, in another embodiment, another number of pairs may be included. Such pair(s) may but need not be opposite to another pair. The loops 122B-1 and 122B-3 in a pair extend in the opposite direction from the other loops 122B-2 and 122B-4. Thus, the loops 122B-1 and 122B-3 curve in the counterclockwise direction while the loops 122B-2 and 122B-4 curve in the clockwise direction. In the embodiment shown, the loops 122C-1 and 122C-3 of a pair 123C-1 and 123C-2, respectively, are mirror images of the other loops 122C-2 and 122C-4, respectively, of the pair 123C-1 and 123C-2, respectively. However, in other embodiments, the loops 122C in a pair 123C may differ.

Each loop 122C-1, 122C-2, 122C-3 and 122C-4 has a radial portion 126C-1, 126C-2, 126C-3 and 126C-4 (collectively or generically 126C), respectively, and an axial portion 124C-1, 124C-2, 124C-3 and 124C-4 (collectively or generically 124C). The radial portion 126C extends substantially radially and is connected to the optic 1120. The axial portion 124C extend substantially in the clockwise or counterclockwise direction. In some embodiments, the axial portion 124C is substantially perpendicular to the radial portion 126C. For example, the angle between the axial portion 124C and the radial portion 126C may be at least seventy degrees and not more than one hundred and ten degrees.

Each loop 122C spans an angle, $\phi C$. Although all loops are shown as spanning the same angle, in some embodiments, the loops may span different angles. Together, the loops 122C span well over ninety degrees (e.g. $4*\phi C \geq \pi/2$). In some embodiments, the loops 122C span over one hundred and eighty degrees ((e.g. $4*\phi C \geq \pi$). Because of their configuration, combined the loops 122C contact the capsular bag over a large angle. Stated differently, the opposing pairs 123C-1 and 123C-2 bear on the capsular bag over a large angle that is opposite to the portion of the capsular bag contact by the other pair 123C-2 and 123C-1, respectively. The capsular bag may thus be extended over a larger volume. This volume may also be more evenly distributed around the optic axis. This may increase stability, reduce striae and, therefore, reduce PCO.

As can be seen in FIG. 3B, the haptic structure 120C includes sharp corners. As a result, the optic 110 may be surrounded on all sides by sharp edges. PCO may be reduced or eliminated by the haptic structure 120C. The IOL 100C may share some or all of the benefits of the IOL(s) 100A and/or 100B. The pairs 123C of loops 122C contact the capsular bag over a larger angle and may be better able to extend the capsular bag. This may improve the stability of the IOL 100C, reduce striae in the capsular bag, and mitigate or prevent PCO. Sharp edges for the closed-loop haptic structure 120C may further reduce PCO. Thus, performance of the IOL 100C may be improved.

Figure 4:
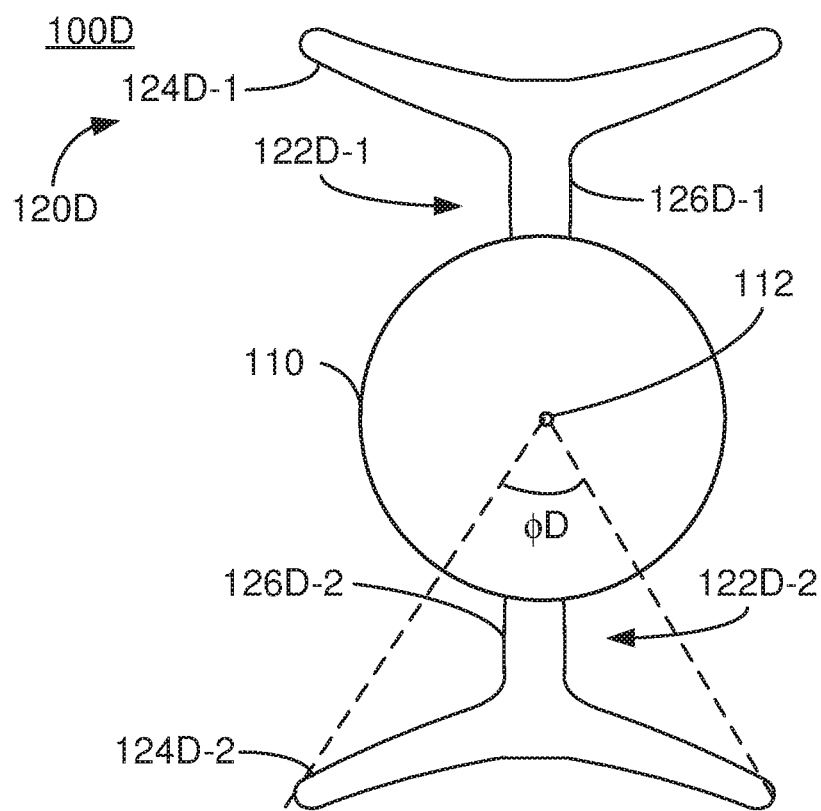
FIG. 4 depicts a plan view of another exemplary embodiment of an ophthalmic device having an open-loop haptic structure.

FIG. 4 depicts a plan view of another exemplary embodiment of an ophthalmic device 100D having an optic 110 and an open-loop haptic structure 120D. For simplicity, the ophthalmic device 100D is also referred to as an IOL 100D. The IOL 100D is analogous to the IOL 100A. Consequently, analogous components have similar labels. Thus, the IOL 100D includes an optic 110 and open-loop haptic structure 120D that are analogous to the optic 110 and open-loop haptic structure 120A. Because optic 110 of IOL 100D is substantially the same as the optic 110 of IOL 100A, the optic 110 of IOL 100D will not be separately described with regard to FIG. 4. For clarity, FIG. 4 is not to scale and not all components may be shown.

In the embodiment shown, the loops 122D are coupled with the optic 110. Thus, a frame analogous to the frame 121A has been omitted. In other embodiments, a frame may be present. In some embodiments, the haptic structure 120D and the optic 110 may be molded together. Thus, the optic 110 and haptic 120D may form a single monolithic structure. In other embodiments, the haptic 120D may be otherwise attached to the optic 110. For example, the loops 122D may be bonded to or molded around a preexisting optic 110.

The loops 122D are transverse loops in that the loops include a base portion and a transverse portion oriented at a large angle from the radial portion. Loop 122D-1 thus includes a base 126D-1 and a transverse section 124D-1. The loop 122D-2 includes a base 126D-2 and a transverse portion 124D-2. In the embodiment shown, the transverse portions 124D-1 and 124D-2 (collectively or generically 124D) are coupled to the bases 126D-1 and 126D-2 (collectively or generically 126D), respectively, at their centers. In other embodiments, this connection point may be shifted somewhat. The transverse portions 124D are also shown as extending outward. In other words, the angle between portions of the transverse section 124D and the base 126D is greater than ninety degrees. Thus, each loop 122D is Y-shaped. In another embodiment, the transverse section 124D may be at substantially a right angle from the base 126D. In such an embodiment, the loop 122D would be T-shaped. In an alternate embodiment, the angle between the transverse section 124D and the base 126D might be less than ninety degrees. However, in general, an angle of at least ninety degrees and not more than one hundred and thirty-five degrees may be desirable.

Each loop 122D contacts the capsular bag (not shown) at the ends of the transverse section 124D. The capsular bag is extended by contact with the four points of the loops 122D.

Each loop 122D spans an angle, φD. Although all loops are shown as spanning the same angle, in some embodiments, the loops may span different angles. Together, the loops 122D span over ninety degrees (e.g. 2*φD≥π/2). In some embodiments, the loops 122D span an angle of at least one hundred and twenty degrees ((e.g. 2*φD≥π/3). Because of their configuration, combined the loops 122D contact the capsular bag over a large angle. The capsular bag may thus be extended over a larger volume. This may increase stability, reduce striae and, therefore, reduce PCO. Although extending the capsular bag via contact with four points of the haptic structure 120D may introduce some striae, these may be unlikely to be at the posterior side of the optic 110. Thus, striae that result in PCO and, therefore, PCO may still be reduced.

The haptic structure 120D may still include sharp corners. As a result, the optic 110 may be surrounded on all sides by sharp edges. PCO may be reduced or eliminated by the haptic structure 120D. The IOL 100D may share some or all of the benefits of the IOL(s) 100A, 100B and/or 100C. The haptic structure 120D may reduce striae in the capsular bag, and mitigate or prevent PCO. Sharp edges for the closed-loop haptic structure 120D may further reduce PCO. Thus, performance of the IOL 100C may be improved.

Figure 5:
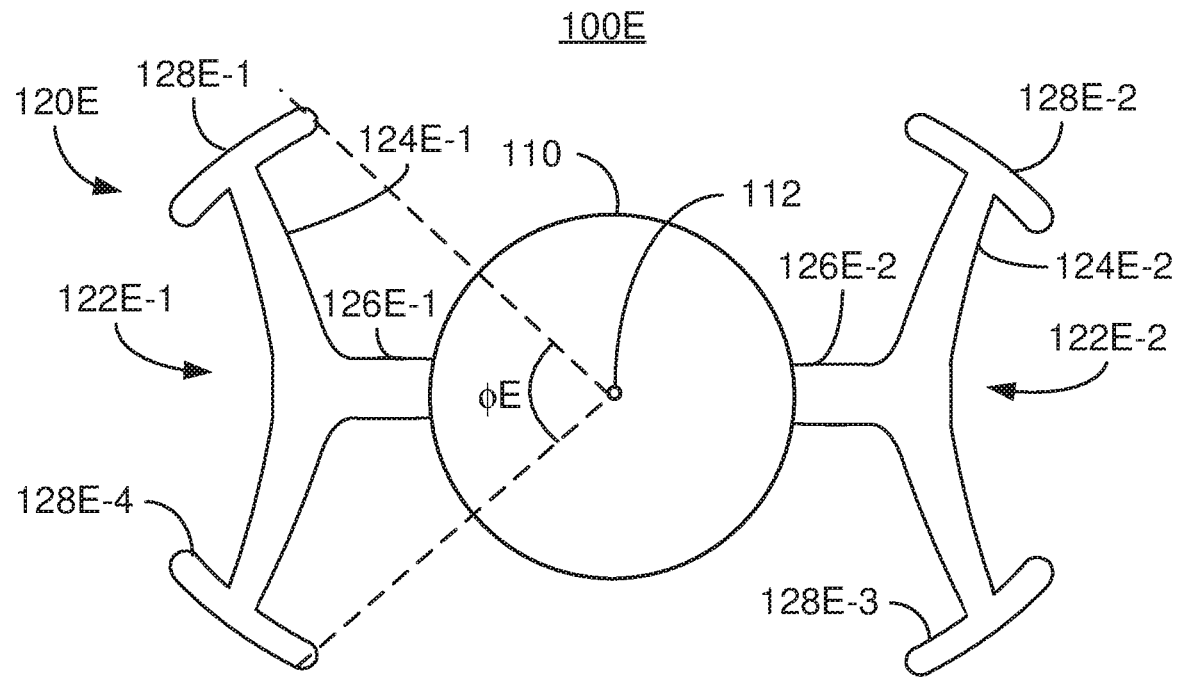
FIG. 5 depicts a plan view of another exemplary embodiment of an ophthalmic device having an open-loop haptic structure.

FIG. 5 depicts a plan view of another exemplary embodiment of an ophthalmic device 100E having an optic 110 and an open-loop haptic structure 120E. For simplicity, the ophthalmic device 100E is also referred to as an IOL 100E. The IOL 100E is analogous to the IOL 100A. Consequently, analogous components have similar labels. Thus, the IOL 100E includes an optic 110 and open-loop haptic structure 120E that are analogous to the optic 110 and open-loop haptic structure 120A. Because optic 110 of IOL 100E is substantially the same as the optic 110 of IOL 100A, the optic 110 of IOL 100E will not be separately described with regard to FIG. 5. For clarity, FIG. 5 is not to scale and not all components may be shown.

In the embodiment shown, the loops 122E are coupled with the optic 110. Thus, a frame analogous to the frame 121A has been omitted. In other embodiments, a frame may be present. In some embodiments, the haptic structure 120E and the optic 110 may be molded together. Thus, the optic 110 and haptic 120E may form a single monolithic structure. In other embodiments, the haptic 120E may be otherwise attached to the optic 110. For example, the loops 122D may be bonded to or molded around a preexisting optic 110.

The haptic structure 120E is most analogous to the optic structure 120D. The loops 122E are transverse loops including a base portion and a transverse portion oriented at a large angle from the radial portion. Loop 122E-1 thus includes a base 126E-1 and a transverse section 124E-1. The loop 122-2 includes a base 126E-2 and a transverse portion 124E-2. The loops 122E, bases 126E-1 and 126E-2 (collectively or generically 126E) and transverse portions 124E-1 and 124E-2 (collectively or generically 1246E) are analogous to loops 122D, bases 126D and transverse portions 124E, respectively.

In addition, the loops 122E include feet 128E-1, 128E-2, 128E-3 and 128E-4 (collectively or generically 182E). Each loop 122E contacts the capsular bag (not shown) at the feet 128E. The capsular bag is extended by contact with the four feet 128E of the loops 122E. Each loop 122E spans an angle, φE. Although all loops are shown as spanning the same angle, in some embodiments, the loops may span different angles. Together, the loops 122E span well over ninety degrees (e.g. 2*φE≥π/2). In some embodiments, the loops 122E span an angle of at least one hundred and twenty degrees ((e.g. 2*φE≥π/3). Because of their configuration, combined the loops 122E contact the capsular bag over a large angle. The capsular bag may thus be extended over a larger volume. This may increase stability, reduce striae and, therefore, reduce PCO. Although extending the capsular bag via contact with four points of the haptic structure 120D may introduce some striae, these may be unlikely to be at the posterior side of the optic 110. Further, use of the feet 128E provide a wider area of contact with the capsular bag and may reduce the probability that striae are formed. Thus, striae and PCO may still be reduced.

The haptic structure 120E may still include sharp corners. As a result, the optic 110 may be surrounded on all sides by sharp edges. PCO may be reduced or eliminated by the haptic structure 120E. The IOL 100D may share some or all of the benefits of the IOL(s) 100A, 100B, 100C, and/or 100D. The haptic structure 120E may reduce striae in the capsular bag, and mitigate or prevent PCO. Sharp edges for the closed-loop haptic structure 120E may further reduce PCO. Thus, performance of the IOL 100C may be improved.

Figure 6:
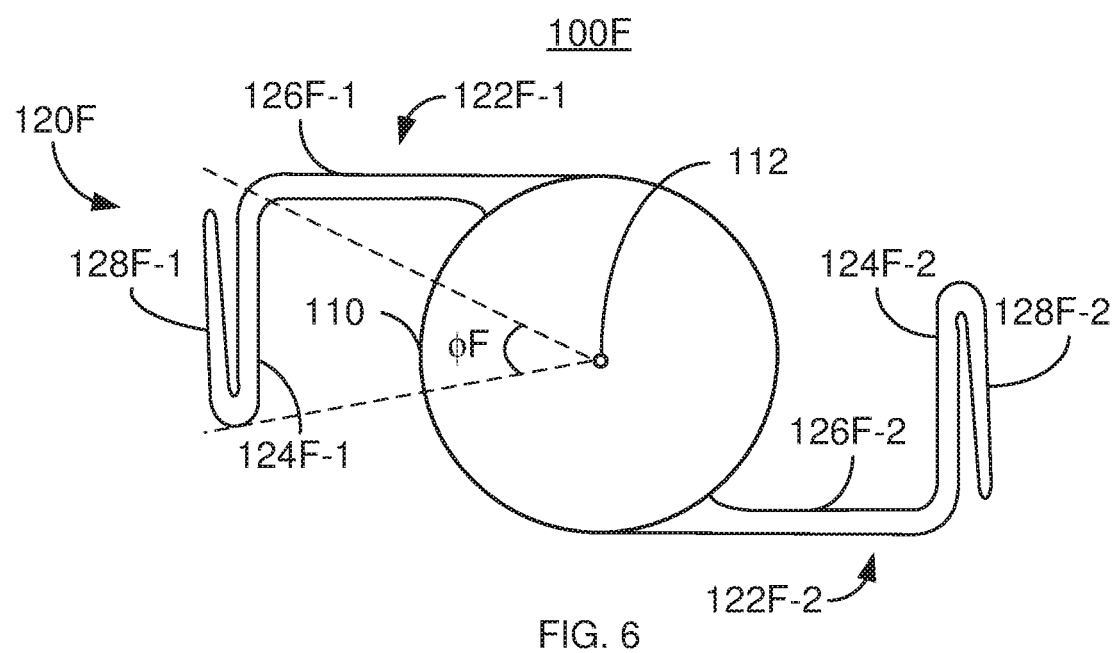
FIG. 6 depicts a plan view of another exemplary embodiment of an ophthalmic device having an open-loop haptic structure.

FIG. 6 depicts a plan view of another exemplary embodiment of an ophthalmic device 100F having an optic 110 and an open-loop haptic structure 120F. For simplicity, the ophthalmic device 100F is also referred to as an IOL 100F. The IOL 100F is analogous to the IOL 100A. Consequently, analogous components have similar labels. Thus, the IOL 100F includes an optic 110 and open-loop haptic structure 120F that are analogous to the optic 110 and open-loop haptic structure 120A. Because optic 110 of IOL 100F is substantially the same as the optic 110 of IOL 100A, the optic 110 of IOL 100F will not be separately described with regard to FIG. 5. For clarity, FIG. 6 is not to scale and not all components may be shown.

In the embodiment shown, the loops 122F are coupled with the optic 110. Thus, a frame analogous to the frame 121A has been omitted. In other embodiments, a frame may be present. In some embodiments, the haptic structure 120F and the optic 110 may be molded together. Thus, the optic 110 and haptic 120F may form a single monolithic structure. In other embodiments, the haptic 120F may be otherwise attached to the optic 110. For example, the loops 122F may be bonded to or molded around a preexisting optic 110.

The loops 122F are rectangular loops in that the loops include a first portion and a second portion oriented at an angle close to ninety degrees from the first portion. Loop 122F-1 thus includes a first portion 126F-1 and a second portion 124F-1. The loop 122f-2 includes a first portion 126F-2 and a transverse portion 124F-2. In the embodiment shown, the second portions 124F-1 and 124F-2 (collectively or generically 124F) are coupled to the first portions 126F-1 and 126F-2 (collectively or generically 126F), respectively, at their ends. In other words, the angle between portions of the second section 124F and the first section 126F is close to ninety degrees. For example, this angle may be at least seventy degrees and not more than one hundred and ten degrees. Together, these sections 124F and 126F may be substantially rectangular in shape.

In addition, each loop 122F-1 and 122F-2 includes feet 128F-1 and 128F-2. Each loop 122E contacts the capsular bag (not shown) at the feet 128F. Together, the loops 122F span over ninety degrees (e.g. 2*φF≥π/2). Because of their configuration, combined the loops 122F contact the capsular bag over a relatively large angle. The capsular bag may thus be extended over a larger volume. This may increase stability, reduce striae and, therefore, reduce PCO. The haptic structure 120F may still include sharp corners. As a result, the optic 110 may be surrounded on all sides by sharp edges.

PCO may be reduced or eliminated by the haptic structure 120F. The IOL 100F may share some or all of the benefits of the IOL(s) 100A, 100B, 100C, 100D and/or 100E. The haptic structure 120F may reduce striae in the capsular bag, and mitigate or prevent PCO. Sharp edges for the closed-loop haptic structure 120DF may further reduce PCO. Thus, performance of the IOL 100F may be improved.

Various features of the IOLs 100A, 100B, 100C, 100D, 100E and 100F have been described herein. One of ordinary skill in the art will recognize that one or more of these features may be combined in manners not explicitly disclosed herein and that are not inconsistent with the method and apparatus described.

It will be appreciated that various of the above-disclosed and other features and functions, or alternatives thereof, may be desirably combined into many other different devices or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An ophthalmic device comprising:
   an optic including an optic axis; and
   an open-loop haptic structure coupled with the optic, the open-loop haptic structure including a pair of open loops, the pair of open loops comprising a first open loop and a second open loop, wherein:
   at least a portion of the first open loop extends in a first angular direction;
   at least a portion of the second open loop extends in a second angular direction, the second angular direction being opposite the first angular direction;
   the first open loop and the second open loop are configured to be compressed by a capsular bag; and
   the second open loop is configured such that an end of the second open loop abuts against a portion of the first open loop between the optic and a free end of the first open loop to prevent further compression of the first open loop when the first open loop and the second open loop are compressed by a capsular bag.

2. The ophthalmic device of claim 1, wherein the first open loop is longer than the second open loop.

3. The ophthalmic device of claim 1, wherein the at least a portion of the first open loop that extends in the first angular direction extends toward the second open loop.

4. The ophthalmic device of claim 1, wherein the open loop haptic structure is coupled to the optic via a frame surrounding the optic.

5. The ophthalmic device of claim 4, wherein the frame comprises a cross-sectional thickness greater than that of an edge of the optic.

6. The ophthalmic device of claim 4, wherein the frame comprises a cross-sectional thickness the same as that of an edge of the optic.

7. The ophthalmic device of claim 1, wherein the second open loop is further configured to prevent the first open loop from collapsing when compressed radially.

8. The ophthalmic device of claim 1, wherein the open-loop haptic structure further comprises a second pair of open loops, the second pair of open loops comprising a third open loop and a fourth open loop, and wherein the fourth open loop is configured to abut a portion of the third open loop between the optic and a free end of the third open loop when the third open loop and the fourth open loop are compressed by the capsular bag.

9. The ophthalmic device of claim 8, wherein the third open loop is longer than the fourth open loop.

10. The ophthalmic device of claim 8, wherein:
    at least a portion of the third open loop extends in the first angular direction; and
    at least a portion of the fourth open loop extends in the second angular direction.

11. The ophthalmic device of claim 10, wherein the at least a portion of the third open loop that extends in the first angular direction extends toward the fourth open loop.

12. The ophthalmic device of claim 1, wherein at least one of the first open loop and the second open loop comprises at least one edge configured to reduce migration of cells.

13. The ophthalmic device of claim 1, wherein the first angular direction corresponds to a counter-clockwise direction, and the second angular direction corresponds to a clockwise direction.

14. An ophthalmic device, comprising:
    an optic; and
    an open-loop haptic structure coupled to the optic, the open-loop haptic structure comprising:
    a first open loop, and
    a second open loop,
    wherein the first open loop and the second open loop are configured to be compressed by a capsular bag, and at least a portion of the second open loop is configured such that an end of the second open loop abuts against a portion of the first open loop between the optic and a free end of the first open loop to prevent further compression of the first open loop when the first open loop and the second open loop are compressed by a capsular bag.

15. The ophthalmic device of claim 14, wherein the second open loop is configured to reduce a radial distance of movement of the first open loop when the first open loop is compressed radially.

16. An ophthalmic device, comprising:
    an open-loop haptic structure configured to be affixed to an optic, the open-loop haptic structure comprising:
    a first open loop, and
    a second open loop,
    wherein the first open loop and the second open loop are configured to be compressed by a capsular bag, and at least a portion of the second open loop is configured such that an end of the second open loop abuts against a portion of the first open loop between the optic and a free end of the first open loop to prevent further compression of the first open loop when at least the first open loop is compressed by a capsular bag.

* * * * *